United States Patent
Song et al.

(10) Patent No.: US 7,894,884 B2
(45) Date of Patent: Feb. 22, 2011

(54) SYSTEM AND METHOD FOR ISCHEMIA CLASSIFICATION WITH IMPLANTABLE MEDICAL DEVICE

(75) Inventors: Zhendong Song, Shoreview, MN (US); Steven N. Lu, Fridley, MN (US); Shailesh K. V. Musley, Blaine, MN (US); Eduardo N. Warman, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 963 days.

(21) Appl. No.: 11/669,357

(22) Filed: Jan. 31, 2007

(65) Prior Publication Data

US 2008/0183086 A1 Jul. 31, 2008

(51) Int. Cl. *A61B 5/02* (2006.01)
(52) U.S. Cl. ............ 600/509; 600/508; 600/521; 128/920; 128/923
(58) Field of Classification Search ......... 600/508–509, 600/521; 128/920, 923
See application file for complete search history.

(56) References Cited

U.S. PATENT DOCUMENTS

| | | | | |
|---|---|---|---|---|
| 5,113,869 | A * | 5/1992 | Nappholz et al. | 600/508 |
| 5,135,004 | A | 8/1992 | Adams et al. | |
| 5,313,953 | A * | 5/1994 | Yomtov et al. | 600/508 |
| 6,112,116 | A | 8/2000 | Fischell et al. | |
| 6,115,630 | A * | 9/2000 | Stadler et al. | 600/521 |
| 6,128,526 | A | 10/2000 | Stadler et al. | |
| 6,501,983 | B1 | 12/2002 | Natarajan et al. | |
| 6,937,899 | B2 | 8/2005 | Sheldon et al. | |
| 2003/0149423 | A1 | 8/2003 | Fischell et al. | |
| 2004/0122478 | A1 | 6/2004 | Stadler et al. | |
| 2004/0215092 | A1 | 10/2004 | Fischell et al. | |
| 2006/0167519 | A1 | 7/2006 | Gil et al. | |
| 2007/0093720 | A1 * | 4/2007 | Fischell et al. | 600/509 |

FOREIGN PATENT DOCUMENTS

EP 0513457 A 11/1992

OTHER PUBLICATIONS

Horacek BM et al. "Electrocardiographic ST-Segment Changes During Acute Myocardial Ischemia," Cardiac Electrophysiology Review 2002(6):196-203 (2002).*
Hanninen H et al. "ST-segment Level and Slope in Exercise-Induced Myocardial Ischemia Evaluated with Body Surface Potential Mapping," Am. J. Cardiol. 2001(8):1152-1156 (2001).*
International Search Report, PCT/US2008/051981, Jul. 28, 2008, 6 Pages.
European Office Action from corresponding European Application Serial No. 08 728 243.0-1265 dated Dec. 4, 2009 (3 pages).
Written Opinion of the International Searching Authority from corresponding PCT Application Serial No. PCT/US2008/051981 dated Jul. 31, 2009 (6 pages).
International Preliminary Report on Patentability from corresponding PCT Application Serial No. PCT/US2008/051981 dated Aug. 4, 2009 (7 pages).

* cited by examiner

*Primary Examiner*—Carl H Layno
*Assistant Examiner*—Deborah Malamud
(74) *Attorney, Agent, or Firm*—Michael J. Ostrom; Stephen W. Baver

(57) ABSTRACT

An implantable medical device monitors ST segment data collected from EGM. ST trends are established and monitored over time. The IMD is able to discern whether the data indicate supply ischemia, demand ischemia, or other physiological causes. The IMD is then able to provide appropriate information and alerts.

32 Claims, 12 Drawing Sheets

SYSTEM AND METHOD FOR ISCHEMIA CLASSIFICATION WITH IMPLANTABLE MEDICAL DEVICE

BACKGROUND OF THE INVENTION

The present invention relates to medical devices and more particularly, to implantable medical devices.

DESCRIPTION OF THE RELATED ART

The heart pumps blood via the arteries to deliver oxygen to all portions of the body. Like any other organ or tissue structure, the heart requires oxygen and includes coronary arteries to facilitate the delivery of oxygenated blood to cardiac tissue. Unlike other organs, a disruption of the oxygen supplied by the coronary arteries often results in discernable electrical parameters. These electrical parameters may indicate ischemia or infarct and may also indicate the relative severity of the event.

A standard, 12 lead surface ECG (electrocardiogram) records electrical signals across multiple vectors and produces a highly accurate representation of cardiac data. Each cardiac cycle is distinctly represented. A P wave is indicative of atrial depolarization, a QRS complex is indicative of ventricular depolarization and a T wave is indicative of ventricular repolarization. The portion of the signal between the QRS complex and the T wave is referred to as the ST segment. An elevation of the ST segment from a relative baseline is typically indicative of a complete and sudden coronary occlusion whereas a depression of the ST segment is indicative of another form of ischemia, such as demand ischemia. For example, a coronary artery may be partially occluded, allowing sufficient blood flow under normal physiological conditions. When physiological demand increases, such as during exercise, the cardiac tissue receives insufficient oxygen, becoming ischemic. Typically, cessation of the activity reduces demand and as the supply becomes sufficient the ischemia resolves and this is indicated by the ST segment returning to the baseline value.

As indicated, the surface ECG provides accurate and detailed information. In addition, the data is often redundant as each channel that is recorded represents the same events as they occur over different vectors. A physician can therefore check multiple channels when evaluating the data for increased reliability and accuracy.

Implantable medical devices (IMD) often include sensors that detect electrical cardiac signals. When collected internally (as opposed to on the surface (i.e., ECG)), these signals are referred to as an electrogram (EGM). Due to their size and placement, the IMD typically will only record data over one or two distinct vectors. Furthermore, the cathode and anode of a given sensing pair may be relatively close together. For example, a tip electrode and a ring electrode on a common cardiac lead sense electrical signals across a small portion of the heart. The device housing may include one or more electrodes. Thus, sensing from e.g., a tip electrode or coil electrode to the housing ("can") electrode provides a vector across a greater portion of the heart. These examples relate to implantable pulse generators (IPGs), often referred to as pacemakers or low power devices and implantable cardioverter/defibrillators (ICDs), often referred to as high powered devices, which may also include pacing functionality. IPGs and ICDs typically include a housing implanted subcutaneously or submuscularly and connected to one or more leads that transvenously enter the heart. Other devices, such as an implantable loop recorder (ILR) are implanted subcutaneously to record data, but do not include leads extending to or into the heart. For example, the Medtronic Reveal™ includes spaced electrodes on the housing. The EGMs collected are extremely useful for numerous reasons; however, they are limited in certain circumstances and do not necessarily provide the same level and types of information as surface ECG data.

DETAILED DESCRIPTION

Figure 1:
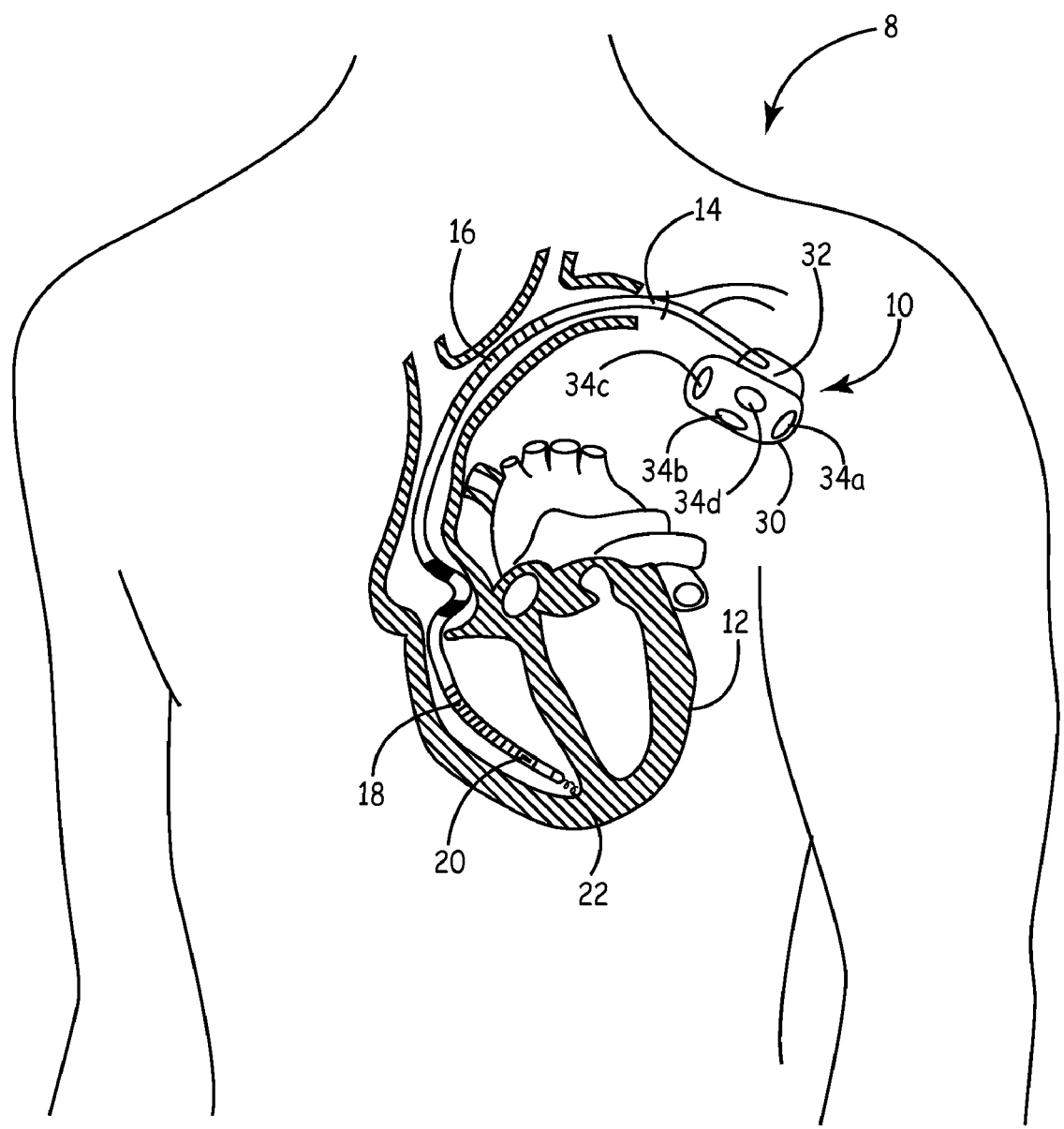
FIG. 1 is a schematic illustration of an implantable medical device (IMD) with a lead extending into a heart.

FIG. 1 illustrates the placement of an exemplary implantable medical device (IMD) 10 within a patient 8. IMD 10 is illustrated as an implantable cardioverter/defibrillator (ICD); however, it should be appreciated that IMD 10 may be an IPG, ILR, drug delivery device, spinal stimulator, neural stimulator, or other implantable device so long as it is capable of sensing electrical cardiac signals. The IMD 10 includes a housing 30 with a header 32 attached thereto. One or more electrodes 34 a, b, c, d (collectively 34) may be included and disposed about various positions on the housing 30; including along an outer perimeter and/or on any portion of a major face of the device including utilizing the entire can as an electrode. A lead 14 is illustrated as being coupled to the housing 30 via the header 32. It should be appreciated that more than one lead may be employed.

The lead 14 enters the vasculature through the superior vena cava (SVC), passes through the right atrium and enters the right ventricle (RV). The lead 14 includes an SVC coil electrode 16, an RV coil electrode 18, a ring electrode 20, and a tip electrode 22. A given lead may include one or more of these electrode or electrodes in other configurations. Any two electrodes may serve as the cathode and anode and provide a vector to obtain EGM data. As previously indicated, a vector from, e.g., the RV coil electrode 18 to one of the can electrodes 34 crosses a large portion of the heart 12.

Figure 2:
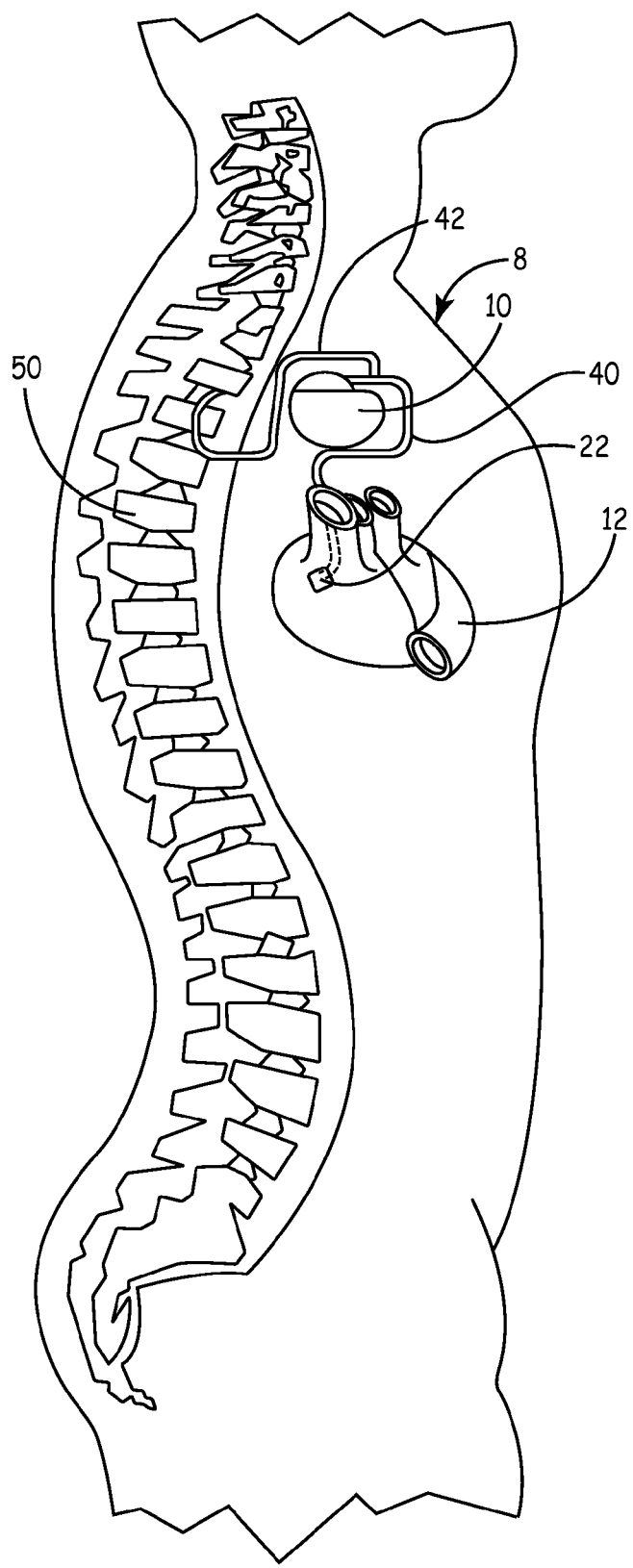
FIG. 2 is a schematic illustration of an IMD having a lead extending into a heart and a lead extending to a spine.

FIG. 2 illustrates another embodiment of IMD 10. In this embodiment, a lead 40 is placed within the heart 12. In addition, a lead 42 is coupled with the patient's spine 50. The lead 42 may deliver electrical stimulation to the spine 50 and/or serve as a mechanism to deliver a drug to the spine 50.

Figure 3:
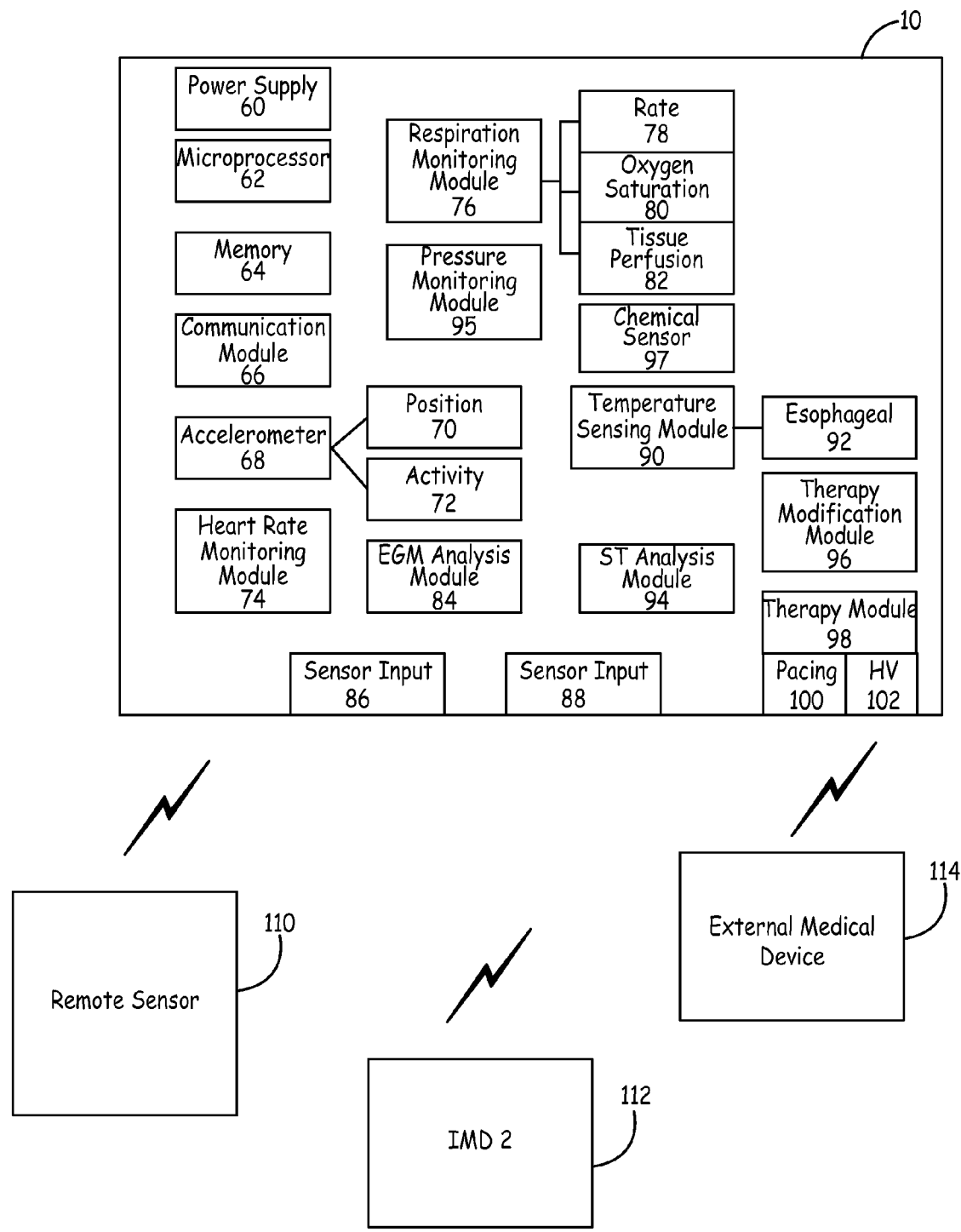
FIG. 3 is a block diagram of selected components of an IMD.

FIG. 3 is a block diagram illustrating various components and/or modules that may be included in any combination in a given IMD 10. Numerous aspects of the IMD 10 are conventional, with many not being illustrated herein and with others not explained in detail. The IMD 10 includes a power supply 60, typically a battery. A microprocessor 62 and memory 64 are included. A communication module 66 is provided so that IMD 10 may communicate via telemetry with an external medical device 114 such as a medical device programmer or other external interface. The communication module 66 also permits communication with remote sensors 110 implanted in other location(s); alternate IMDs 112 implanted in other locations (e.g., a drug pump); or patient worn or carried external devices, sensor, or inputs.

The IMD 10 may include an accelerometer 68 (or multiple accelerometers) that can be configured to provide positional data (e.g., prone, standing, etc.) and/or activity level data 72. A heart rate monitoring module 74 is illustrated. EGM data can readily be utilized to obtain heart rate data and the module 74 illustrates the software, hardware, and/or firmware to provide this data. A respiration monitoring module 76 is provided to generate data related to breathing parameters. An impedance based sensor may be used to measure impedance changes through the chest cavity to establish breathing. Breath rate is output from rate module 78. Sensors may be provided to determine effects of respiration via an oxygen saturation module 80 or tissue perfusion module 82.

An EGM analysis module 84 is provided. This module analyzes EGM data to, in particular, establish ST segment patterns as will be described in greater detail. Sensor inputs 86 and 88 simply illustrate the input of a one or more data sources into the IMD 10. For example, a sensor input may be a lead coupled to the device, an electrode coupled with the device, or some other sensor. A given IMD 10 may include numerous sensor inputs. The IMD 10 is illustrated as having a temperature sensing module 90 and in particular an esophageal temperature sensing module 92. Various internal temperatures may be monitored from that of blood within the heart to temperature changes made by ingesting food or fluids through the esophagus. A pressure sensing module 95 senses fluid pressure within various anatomical locations, such as within a portion of the heart. A chemical sensor 97 may be provided that senses the presence or quantity of a particular substance such a potassium, C reactive protein, or other substances. Working with the EGM analysis module is an ST analysis module 94 that further utilizes EGM data to establish, evaluate and utilize ST segment data.

As will be explained in greater detail, the ST segment data may indicate various physiological conditions. Some of these conditions may warrant implementing or changing a therapy provided by the IMD 10 (if any). Therapy module 96 modifies the therapy parameters based on the indicated data, independently or via instruction from a clinician. If the IMD 10 has a therapy capability, it is represented by the therapy module 98, which may include, for example, a pacing module 100 and/or a high power module 102 for defibrillation.

Figure 4A:
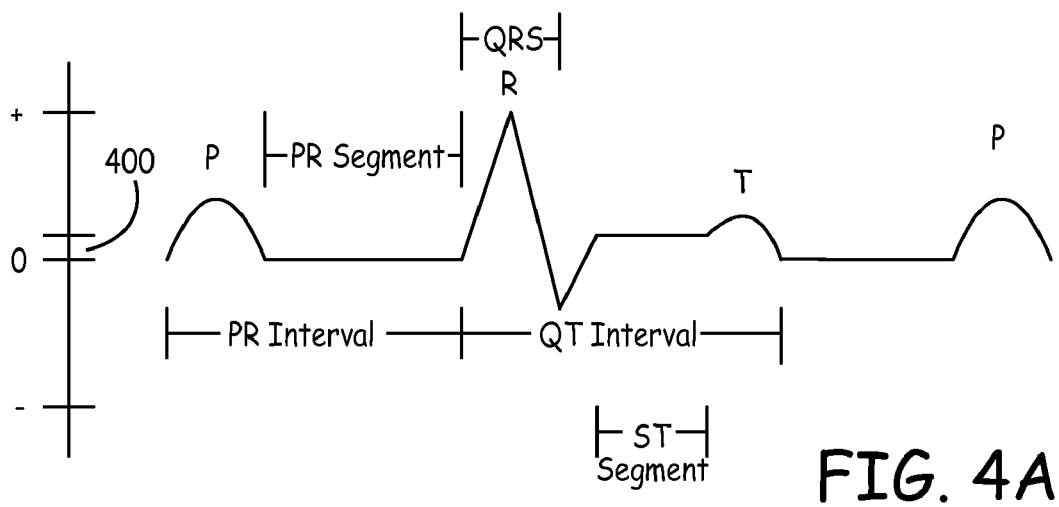
FIGS. 4A-4C illustrate exemplary ECG tracings.
Figure 4B:
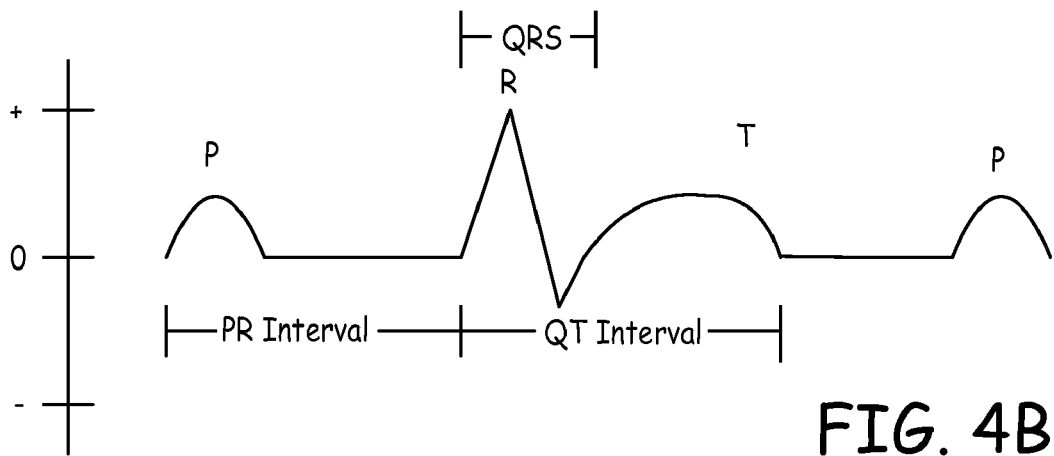
Figure 4C:
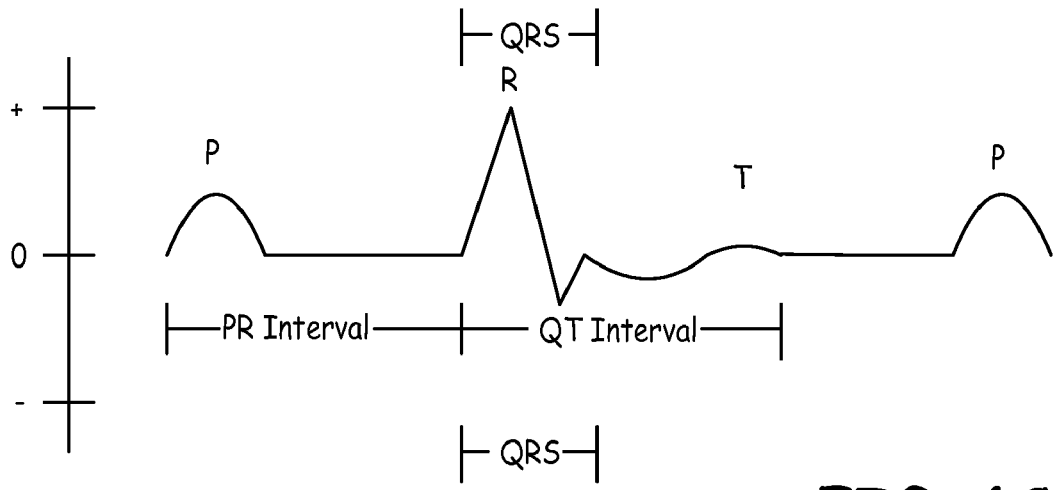

FIGS. 4A-4C are stylized ECG tracings illustrative of various cardiac cycles. FIG. 4A is meant to nominally illustrate a "normal" cardiac cycle. As previously indicated, the P wave is a representation of atrial depolarization. After an AV delay, ventricular depolarization begins, which is indicated by the QRS complex. Finally, the T wave is indicative of repolarization of the ventricles. The various intermediary sections may be represented differently depending upon convention. The PR Interval is shown as beginning with initiation of the P wave and terminating with initiation of the QRS complex. While readily apparent in these stylized representations, such delineation is not always so readily apparent in reality. The isoelectric portion between the P wave and the QRS complex is referred to at the PR segment. The QT interval begins with initiation of the QRS complex and ends with termination of the T wave. Often, the QRS complex is referred to as an R wave; particularly when sensed internally as this is the dominant component. Furthermore, the peak of the R wave is an identifiable marker that will be referred to hereinafter.

The ST segment begins with the termination of the QRS complex and ends with the initial deflection of the T wave. Normally, the ST segment is isoelectric. There may, however, be a difference or delta between the values of the PR segment and the ST segment and is referred to as the ST deviation 400. The ST deviation 400 should be relatively constant; that is, factors that would shift the PR segment will similarly shift the ST segment.

FIG. 4B is a stylized ECG tracing illustrating an elevation in the ST segment as compared to FIG. 4A. Such an elevation is an indicator of potentially serious ischemia or infarct. That is, when a complete coronary occlusion occurs, there is an elevated ST segment. Thus, hospitalization and invasive and/or pharmacological therapy may be warranted.

FIG. 4C illustrates ST segment depression. ST segment depression is a less specific indicator and may relate to demand ischemia or other relatively stable conditions that do not necessarily require immediate intervention. For example, a partially occluded artery may permit sufficient blood flow under normal physiologic conditions. With increased demand, e.g., during exercise, this artery does not provide for the increased oxygen needs of the relevant portion of the heart. As such, that portion of the heart is ischemic; however, upon cessation of the activity the demand is reduced and the ischemia resolves. In such cases, the patient may be monitored, advised to alter activities, or given various drug therapies.

As indicated, these are stylized representations. True ECG tracings are more complicated to evaluate and require some skill on the part of the clinician. Furthermore, with a 12 lead ECG there are multiple channels to evaluate. Thus, if one vector does not clearly demonstrate a parameter, another may. In addition, the multiple vectors can aid in confirming an evaluation.

Figure 5:
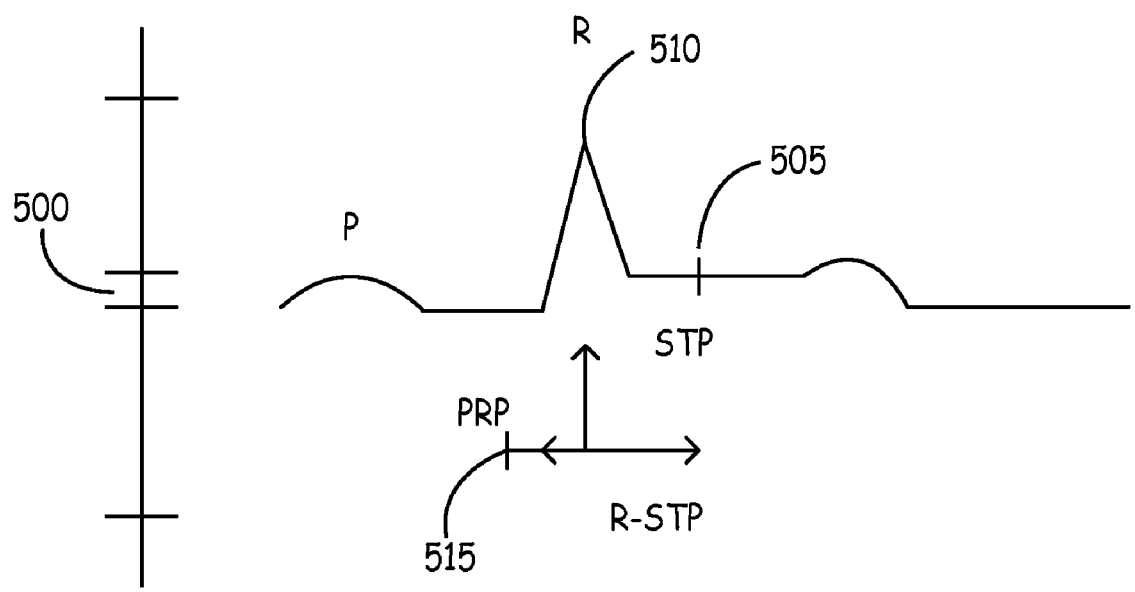
FIG. 5 illustrate an EGM tracing.

FIG. 5 is a stylized representation of an electrogram (EGM), which is a representation of the electrical cardiac signal sensed by an implantable device (such as IMD 10). IMD 10 may include multiple electrodes disposed in various positions. At the very least, the IMD 10 will include at least two electrodes spaced sufficiently far apart that cardiac events are sensed. As indicated, a therapy device such as an IPG or ICD that includes leads provides multiple electrode positional opportunities with spatial diversity. A subcutaneous implantable loop recorder may have a limited number of integral electrodes, positionally limited by the dimensions of the device housing. As such, device positioning upon implant will affect the signals sensed.

The EGM of FIG. 5 is meant to illustrate a normal cardiac cycle like that of FIG. 4A. The P wave is illustrated; however, it should be appreciated that due to the relatively small amplitude of this waveform, it may not be apparent in many EGMs. The R wave is a dominant feature and is typically identifiable, with varying degrees of detail regarding the overall QRS complex. The T wave, like the P wave may or may not be discernable.

The EGM does illustrate a delta between the PR segment and the ST segment, which is ST deviation 500. Though not illustrated, the various ischemic events will produce changes in the EGM; however, these changes do not necessarily correlate to their counterparts in an ECG. That is, if in a given cycle the ECG would indicate ST segment elevation the EGM may or may not indicate the same, may indicate depression, or may not present a discernable change in a given cycle. Thus, the same general "rules" that apply to ECG analysis may not apply to EGM analysis. Thus, sensed ST segment elevation may not reliably indicate a serious condition and ST segment depression may not reliable indicate a less serious condition and may in fact occur due to the more serious condition.

As will be discussed in further detail, embodiments of the present invention utilize trend information about ST segments over multiple cardiac cycles. FIG. 5 illustrates several factors used to identify the relevant ST point 505 (STP) and controls for normal variations. The peak 510 of the R wave is identified as a reference point. A predetermined period of time R-STP (e.g., 80, 90, or 100 ms) is added to the peak 510 to calculate the ST point 505. In other words, the R wave of the QRS complex is identified and using known cycle parameters, a (heart rate modulated) period of time is added so that the selected ST point 505 likely falls within the ST segment. It should be appreciated that various other mechanisms may be utilized instead in order to label this point, such as adding a period of time to the end of the QRS. For example, an analysis of QRS width may be done for each cycle or periodically in order to determine a patient specific value to add to the determined peak. Alternatively, the subsequent P wave may be discernable and time subtracted from this event. The ST point 505 simply needs to be a point that falls within the ST segment with sufficient reliability and any mechanism that achieves this is acceptable.

As previously indicated, there may be isoelectric ST deviation 500 relative to the PR isoelectric level. Thus, embodiments of the present invention also identify a PR point 515 (or PRP). Again, this is simply a point that occurs in the isoelectric segment between the end of the P wave and the initiation of the QRS complex. In one embodiment, points are selected moving backwards from the peak 510 until a determined slope is zero or two temporally separate points have substantially the same value. Alternatively, a predetermined value (of time) is subtracted from the peak 510, again with reasonable reliability that the PRP will be within the PR segment.

Once the PRP is determined, the measured electrical value (milivolts) is subtracted from the measured STP. Thus, the resultant ST point is taken from an isoelectric baseline so that collected data points correlate. A given measured ST point will be referred to as a measured STP and a given ST point correlated with the isoelectric baseline will be referred to as a correlated STP.

Figure 6A:
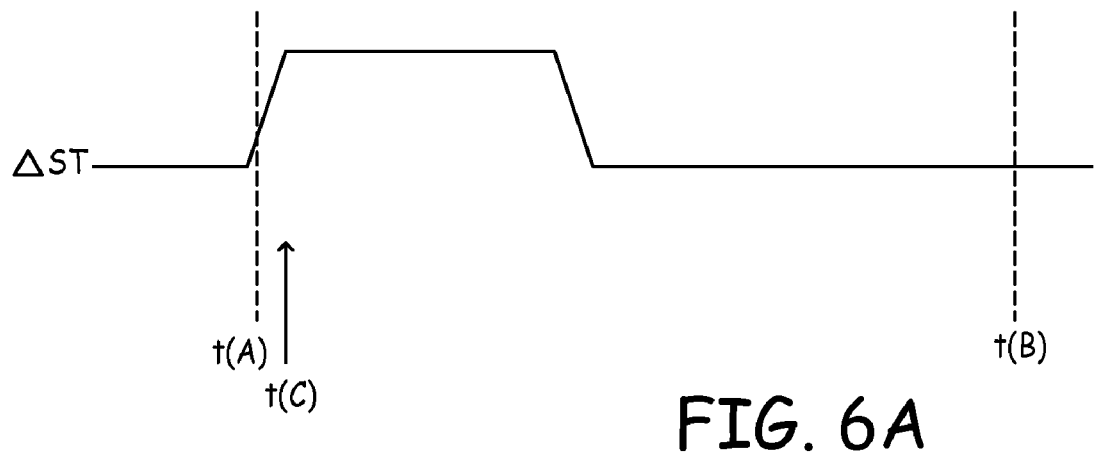
FIGS. 6A-6D illustrate ST variations obtained from EGM data.
Figure 6B:
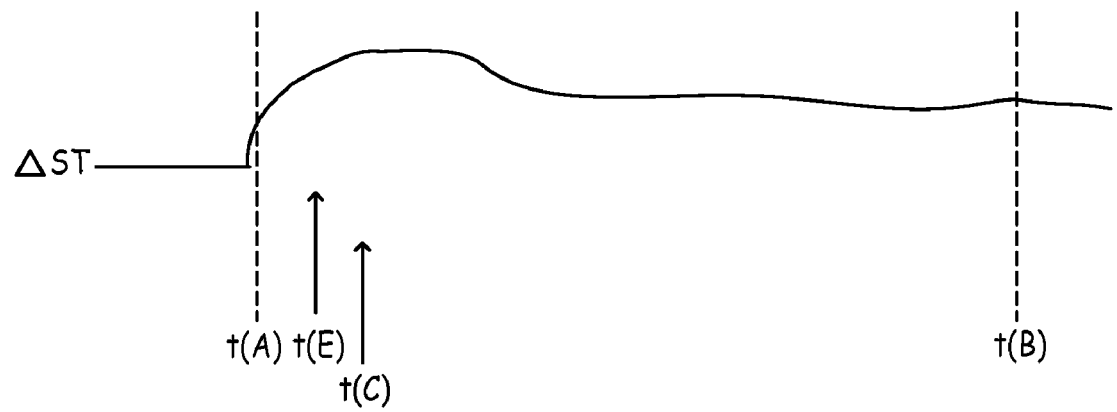
Figure 6C:
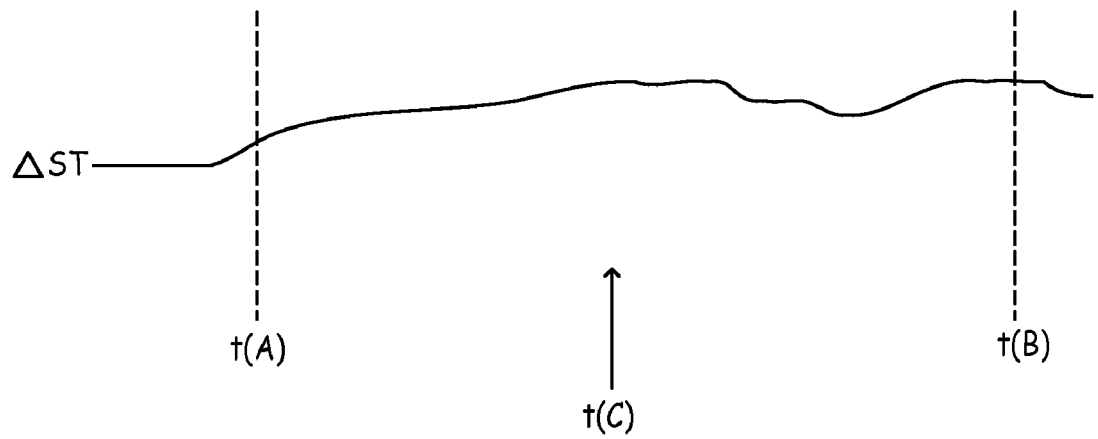

Correlated STPs are collected over time and analyzed. This analysis illustrates trends that are then used to identify clinical events. FIGS. 6A-6C illustrates graphs of the collected correlated STPs over time. In these figures, time t(A) is the time at which the correlated STP exceeds a threshold value. The correlated STPs are either absolute values of the data point or alternatively (and not illustrated) if negative values arise, then the graph is inverted and threshold crossings, maximums, etc. are correspondingly inverted. When the threshold is crossed at t(A), a timer is initiated and runs until time t(B). This defines a period of time of analysis. In one embodiment, this period of time is approximately 10 minutes. At time t(C), the correlated STP reaches a maximum value (relative to the time period t(A) to t(B)).

The graph of FIG. 6A represents a non-ischemic ST segment variation. For example, posture changes may have an effect on ST values. The characteristics of this type of event include a large slope; that is the maximum is reached quickly. The resultant correlated STP holds steady for a given period of time. In other words, an event occurs that very rapidly changes ST values from one relatively steady state to a different, relatively steady state. Similarly, a very rapid change occurs returning the correlated STPs to their baseline values.

FIG. 6B is a graph that represents a serious, sudden onset supply ischemia (e.g., occlusion of a coronary artery) that if untreated (or does not resolve itself) will lead to an acute myocardial infarction (AMI). This is potentially a very serious condition and warrants identification. Exemplary algorithms for determining the nature of the apparent ischemia will be discussed below. A general description begins again with the correlated STP crossing the threshold. The threshold is a value below which variation in the correlated STP is considered normal. That is, while illustrated as a constant baseline, the correlated STPs may have some variation, or noise, without indicating a problem. While non-limiting, the threshold in one embodiment is 0.1 mv.

At time t(A) the correlated STP exceeds the threshold and the timer (running until t(B)) is initiated. This represents the period of time that will be evaluated and after which a conclusion will be drawn. At time t(C), the correlated STP reaches a maximum value (for the interval between t(A) and t(B)). The maximum should be reached relatively quickly to evidence an occlusion but not so quickly as to indicate an innocuous event such as a posture change. After reaching the maximum, the correlated STP levels should remain relatively high through t(B), though they may drop somewhat and still be considered indicative. If the correlated STPs return to their baseline values (or close thereto) at or before time t(B), this likely indicates one of two things. Either, this event was a vasospasm where for some reason the artery constricted itself for a brief period of time and then relaxed or there was a coronary occlusion that resolved itself. Both instances may be notable events that should be recorded and presented to a physician. The later event, i.e., a self resolving coronary occlusion is likely indicative of a clot or plaque that occluded the artery then passed through. This material remains in the arterial system and may present a risk of thrombosis. In general, if the correlated STPs reach a maximum relatively quickly and remain deviated, this is taken as an indication of ischemia caused by a sudden coronary occlusion that will likely lead to an acute myocardial infarction.

FIG. 6C a non-specific ischemia. Notably, the values from the baseline may be positive or negative again illustrating that a comparison with surface ECG deflection or elevation is may or may not be reliable. Here, the values gradually rise to reach a maximum. Though not dispositive and not illustrated to scale, this maximum value is likely less than the maximum of e.g., FIG. 6B, although necessarily greater than the threshold value. FIG. 6C also illustrate some fluctuation after reaching the maximum and though not illustrated, the values may continue to increase after time t(B). This indicates that a non-specific ischemia may be occurring as a result of a drug, a chemical imbalance (e.g., potassium deficiency), or the like.

Figure 6D:
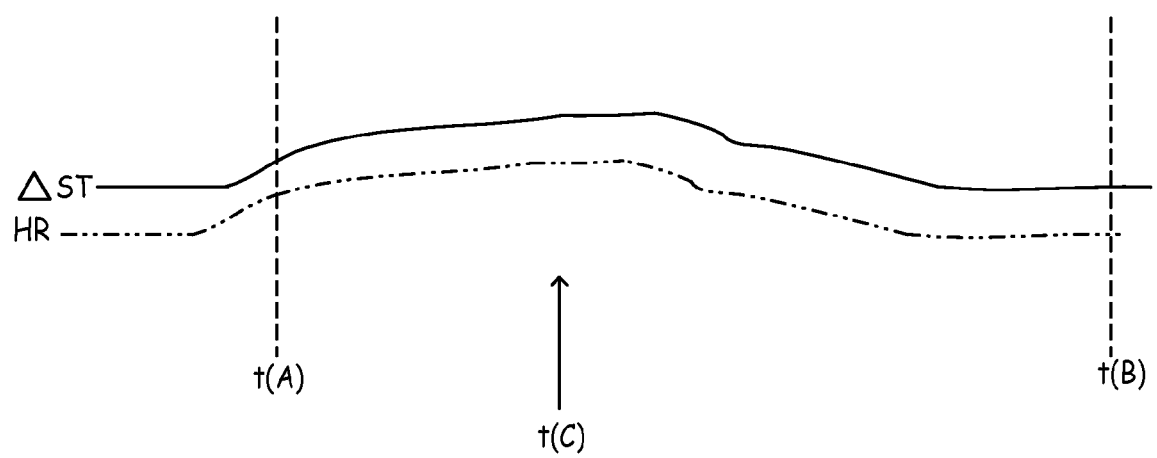

FIG. 6D similarly illustrates a non-specific ischemia wherein the maximum is reached later in the time period t(A) to t(B), thus differentiating it from supply ischemia. Further, the values return to baseline in a relatively short period of time. The evaluation period t(A) to t(B) is in one example, 10 minutes. Demand ischemia occurs if a patient having a partial occlusion increases their level of exertion, such as during exercise. As exertion increases, the body demands more oxygen and the heart works harder. In a similar fashion, the heart then demands more oxygen, which the partially occluded artery cannot supply. The resultant ischemia causes angina and other discomfort to a level that precludes the patient from continuing at that level of exertion. As such, the patient will return to a lesser level of exertion, and the ischemia will resolve. This is illustrated in FIG. 6D along with an exemplary graph of heart rate. In this scenario, the change in ST values will correspond or track with heart rate.

Figure 7:
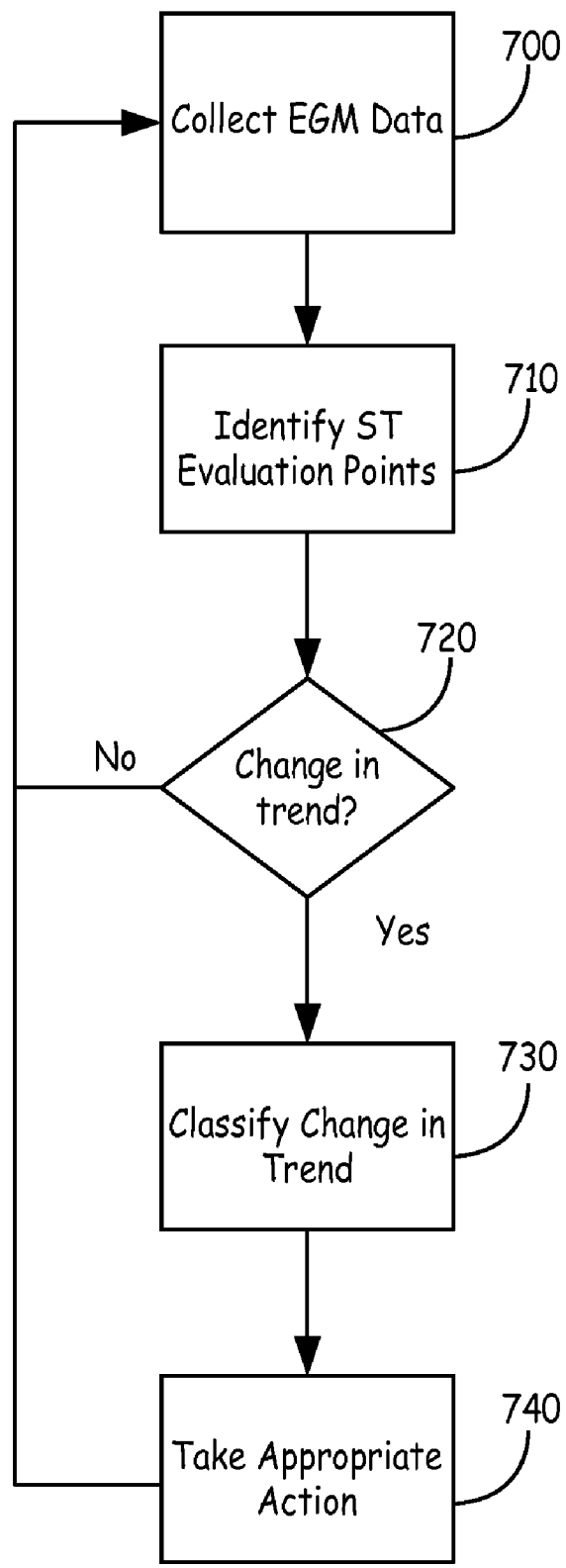
FIGS. 7-10 are flowcharts of processes consistent with the teaching of the present invention.

FIG. 7 is flowchart describing one process consistent with the teachings of the present invention. As previously described, surface ECG and internal EGM signals are both obtained from cardiac electrical data. However, while these signals both relate to the same physiological event (e.g., ventricular depolarization) they do may or may not both be present the same or even necessarily corresponding data. An IMD 10 collects (700) EGM data for each of a plurality of cardiac cycles and at least temporarily stores this data in memory. For each cardiac cycle, the IMD 10 identifies (710) a point within the ST segment for evaluation (STP). These points are compared and the IMD 10 determines if there has been any change (720) in trend beyond a baseline or noise value. If no change (720) is noted, then the IMD 10 simply continues to collect data (700). If a change is noted (720), then this trend data is classified to determine what the trend data indicates such as, for example, a non-ischemic event, demand ischemia, or supply ischemia. Based upon the classification (730), the IMD 10 will take (740) the appropriate action. Such actions may include without limitation doing nothing, noting the event, recording data into memory, alerting the patient, alerting a caregiver, or providing therapy.

Figure 8:
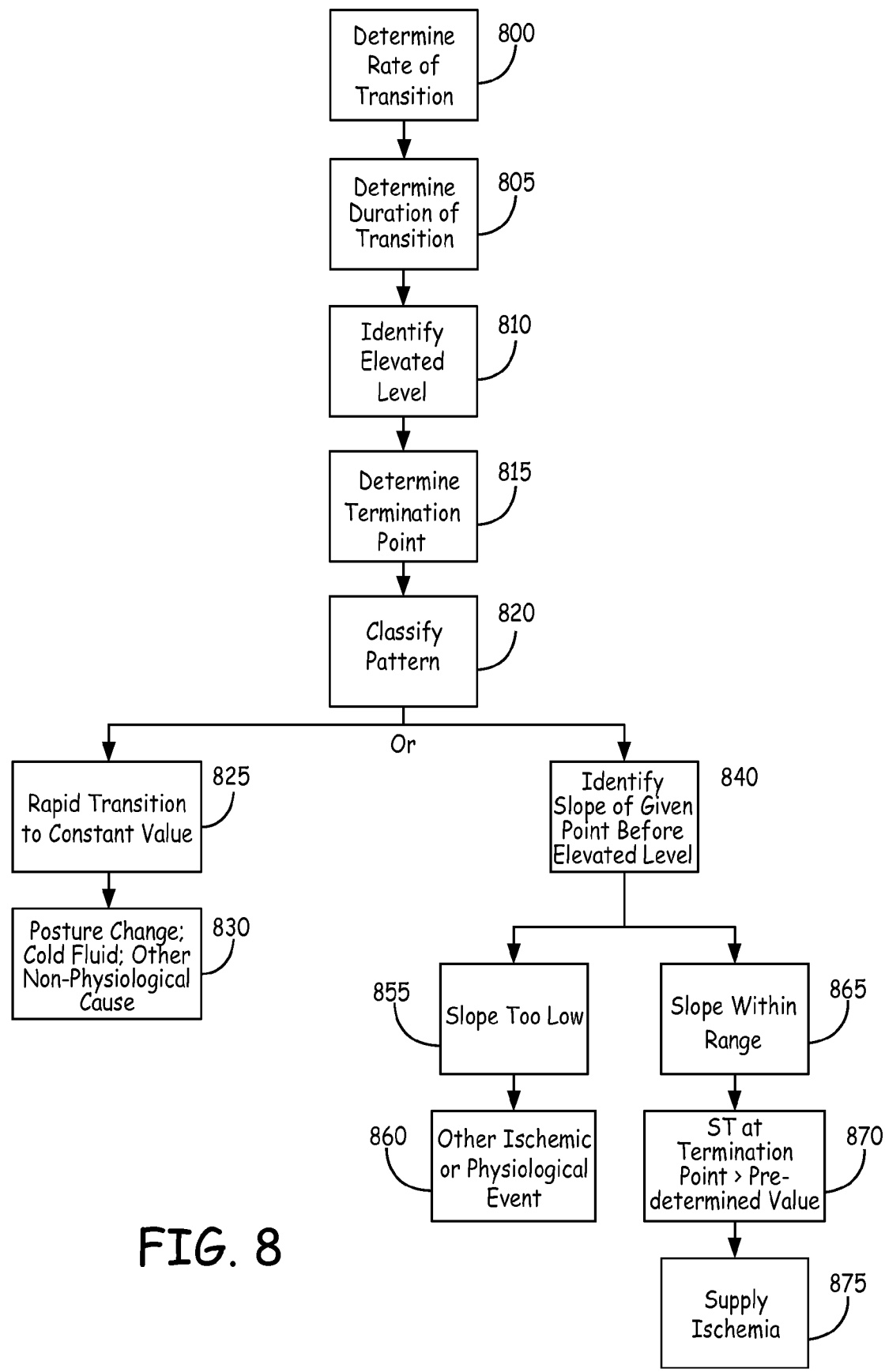

FIG. 8 is a flowchart that describes another process consistent with the teachings of the present invention. In steps 800-815 data is gathered and a pattern is classified at step 820; however, the process of classifying the pattern occurs in steps 825-875 based upon the collected data. It should be further appreciated that the data collected (800-815) is not necessarily collected or processed sequentially nor necessarily in the order presented. Various STPs are collected and a given value crosses a threshold to initiate a relevant time period. From the initiation of the time period until a maximum STP value (during the time period) is reached, the rate of transition or slope of the transition is determined (800). In addition, the time from initiation until the maximum is reached is determined (805). In other words, how long does it take to reach the maximum STP, once the period is initiated. The correlated ST value of the maximum value is identified (810). This is the correlated ST value. The termination point is identified (815). This is not necessarily a separate step as the initiated time period is for a predetermined duration; hence, this point in time is therefore predetermined. The correlated ST value at this endpoint (or the average value of several points before, during and after this endpoint) is noted.

Once these data points are determined, the pattern is classified (820). In a first branch, the duration of the transition (805) is too short (825). That is, the time interval from initiation of the time period until reaching a maximum is too fast to be physiologic. Furthermore, if this branch is followed, the rapid transition is typically followed by a relatively constant rate. Thus, causes for this type of pattern may be an abrupt change in posture or the sudden ingestion of a cold fluid. The specific timing parameters are not meant to be limiting in the present description and there may be some overlap at boundary conditions (which may be further analyzed as described hereinafter). As a general guideline, a rapid transition that ranges from nearly instantaneous to a few seconds is "too" rapid to be ischemic. Transitions that extend to, for example, 30 seconds are likely too rapid. Again, non-ischemic causes will tend to be very rapid and abrupt such as a posture change. Typically, this should present a very discernable temporal relationship that would not require subsequent analysis.

If the duration of the transition (805) is greater than a predetermined value, then analysis proceeds along branch 840. Here, a point prior to the maximum is identified. This may be a predetermined number of data points prior to the maximum, the time at which a predetermined percentage of the maximum is reached (e.g., 50%, 90%), or a time based identifier such as one half or three quarters of the duration (805). This is meant to uniformly identify some point along the transition wherein taking the slope of this point will provide useful data. For example, once the maximum is reached the slope is likely 0, close to 0, or even negative. Thus, step 840 identifies a point prior to the maximum wherein the slope is taken and utilized.

If the slope is too low (855) this indicates demand ischemia (860) or some other non-physiological cause and this classification is made (820). In other words, the rate of change is too slow to indicate supply ischemia. Conversely, if the slope falls within an indicative range, then the correlated ST value at termination point is evaluated. If this value is above a predetermined threshold, then the pattern is classified as supply ischemia (875). If the value at the termination point is close to the baseline value, then this indicates either a coronary occlusion that self-resolved or vasospasm. Both events may be notable, but are distinct from a classification of supply ischemia.

Figure 9A:
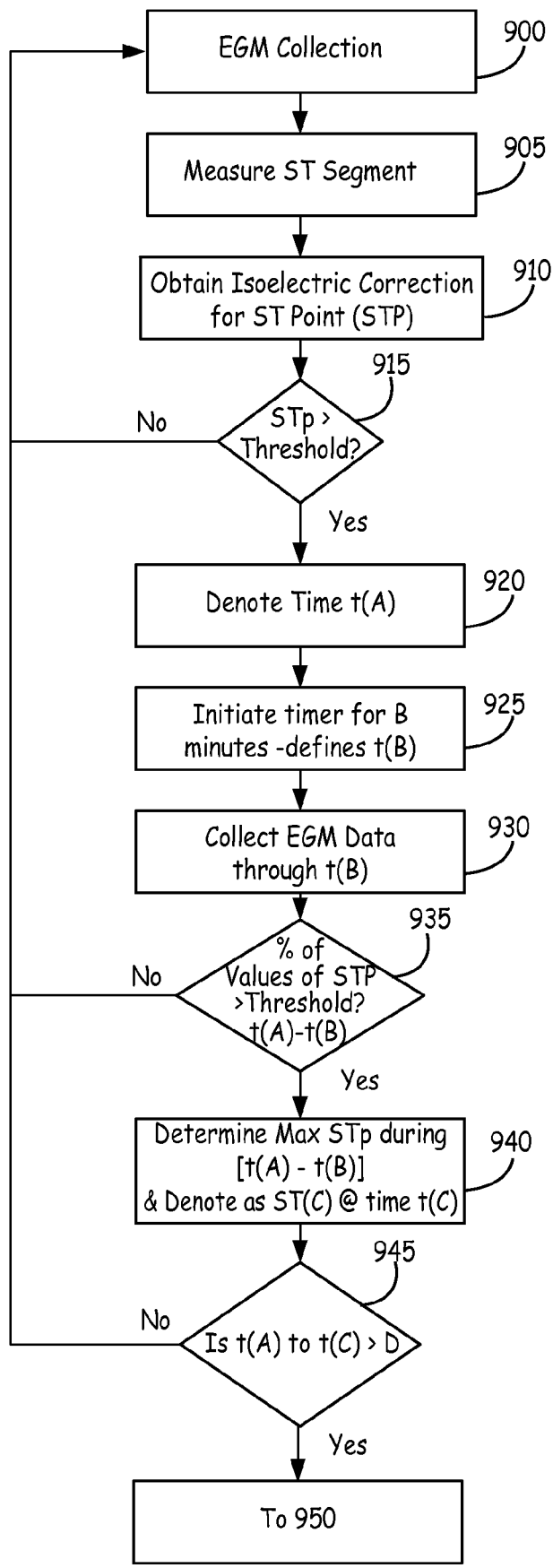
Figure 9B:
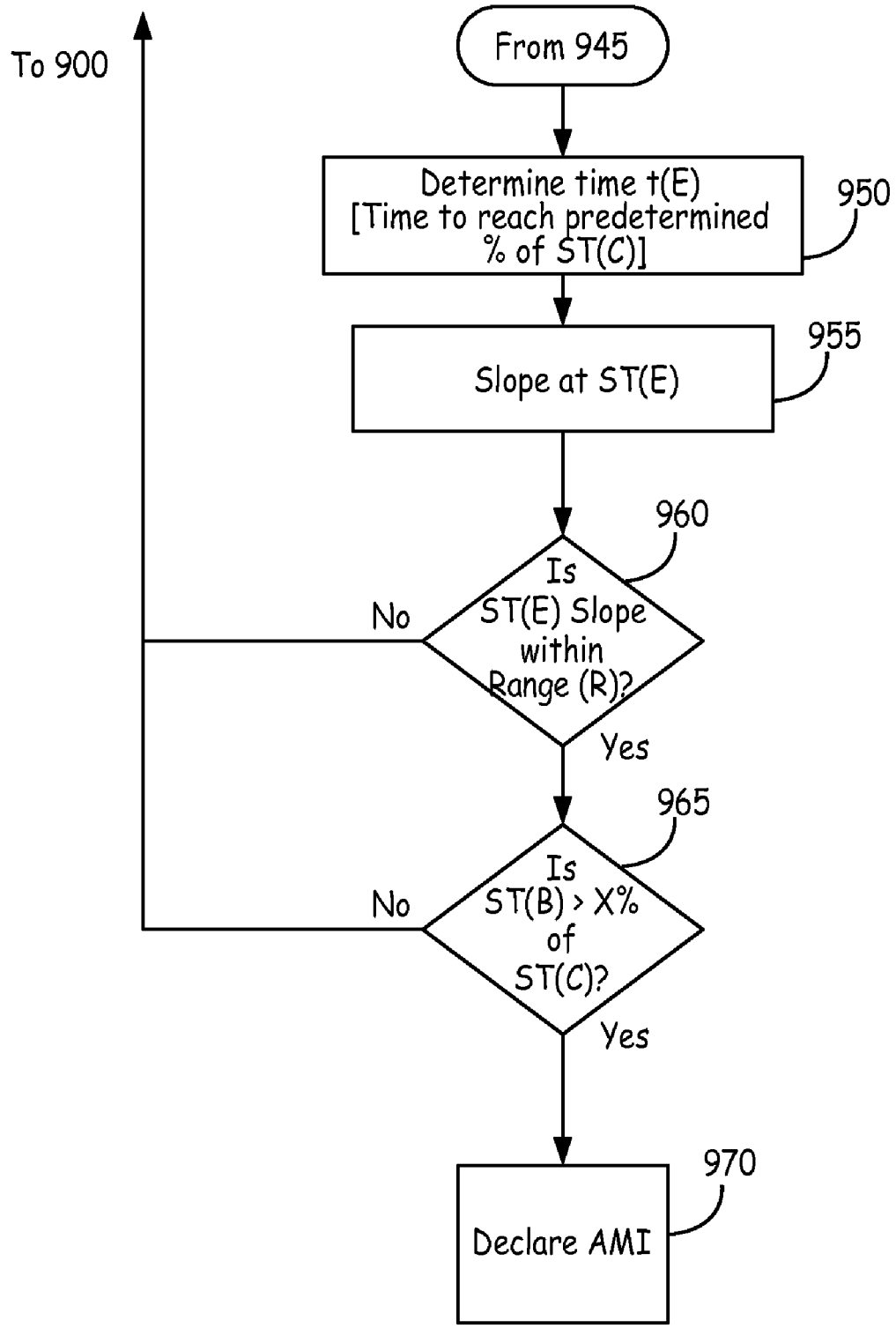

The description of parameters has been rather generalized to illustrate the broader concept and to illustrate that specific numerical limitations will vary based upon the selected evaluation parameters. FIGS. 9A and 9B present a more specific process consistent with the teachings of the present invention. In general, identifying the cause of patterns in the STP is useful whether it is determining a non-ischemic cause such as a posture change or a stable condition such as demand ischemia. The most urgent condition is supply ischemia, which if left unresolved will likely lead to an acute myocardial infarction. Thus, the present process is described in the context of ruling supply ischemia in or out as the primary concern. The flowcharts of FIGS. 9A and 9B will be described with reference to the graphs of FIG. 6A-6D.

In the course of normal operation of the IMD 10, EGM data is collected (900) and processed. As previously explained, an ST data point is identified for each (or once every several) cardiac cycle. This may be a single point taken for each cycle or a number of points/measurements taken during the ST segment and averaged together. The ST data for each cycle is correlated to the baseline value by accounting for the ST deviation from the PR segment, which results (910) in the ST point (STP). As ST segment elevation or depression is not meaningful in the present context, the values may be used as they are taken or absolute values may be utilized.

The STP is compared (915) with a threshold value that is in excess of what would be standard fluctuations or noise. While non-limiting, the threshold in one embodiment is 0.1 mv. If the STP is below (915) the threshold, then the process returns and continues to collect EGM data (900). If the STP exceeds the threshold (915), then the time of this threshold crossing is denoted (920) at t(A) and a timer of B minutes is initiated (925) which will terminate at time t(B). In one embodiment, the timer is run for 10 minutes. The use of a timer is not mandatory, but allows for a specified endpoint and duration.

During the interval from t(A) to t(B), EGM data is collected (930) and processed in the same manner as in steps 900-910 so that an STP is provided for each cardiac cycle. Each of these STPs is evaluated to determine (935) if they all exceed the threshold value. In general, if the STP falls below the threshold value subsequent to initiating the timer, this is an indication that the event was either not supply ischemia or was supply ischemia that self resolved. Thus, if the STP does drop below the threshold during the timer, the process reverts to normal data collection (900). It should be appreciated that this may occur during the running of the timer (925) in which case the entire process in truncated or data is collected during the entire interval and all collected data is evaluated with a conclusion drawn at this point in the process. Further, a certain percentage of the data points may need to be below the threshold for the process to conclude that there is not supply ischemia. For example, if 90% or more of the data points exceed the threshold value, this may satisfy this step (935). If, for example, 80-90% exceed the threshold then the process might evaluate secondary factors rather than reaching a determination, whereas if less than 80% of the values exceed the threshold then a determination that supply ischemia is not present or ongoing is reached.

Assuming all or a sufficient number of STPs during the time period exceed the threshold, then the maximum STP during this time period is identified (940). The time that this maximum value is first reached is denoted t(C). Next the interval from t(A) to t(C) is calculated and compared with predetermined value D (945). If t(A) to t(C) is less than D, then this overall change is too rapid to be supply ischemia and therefore the process concludes that there is no ongoing supply ischemia and returns to generally monitoring (900). Again, this is not necessarily a literal return in that data is being collected; however, the conclusion is reached and the process is not attempting to continue to determine supply ischemia with this data set. The value D is a time duration that would likely result from factors such as posture change and the like that produce rapid transitions. Thus, while non-limiting such durations are likely on the order of a few seconds.

Assuming that the interval from t(A) to t(C) exceeds value D, then the process proceeds to step 950 in FIG. 9B. At this point, the process is generally attempting to discriminate between supply or demand ischemia, which will be primarily differentiated by the slope of the transition prior to reaching the maximum. Taking the slope at the maximum or immediately prior thereto might not produce meaningful data. Thus, another point E is identified. Point E occurs at the time t(E) (between t(A) and t(C)) when the STP reaches a predetermined percentage of the maximum value. For example, when the STP is 90% of the maximum STP, this point is denoted as E and the slope is determined (955).

The slope or rate of change between t(A) and t(E) is evaluated and compared (960) with a predetermined value. If the slope exceeds this value, then the event is not likely to be supply ischemia. As a practical matter, this is the same or similar to that analysis at step (945). If the slope too low, then the rate of change is more indicative of demand ischemia. Again, the specific values may be patient specific or population specific. The rate of change corresponding to an increase in demand due to exercise may likely take approximately two minutes or more to reach a maximum.

If the slope is within the range (960), the final general criteria is whether the STP at t(B) is sufficiently high to indicate (965) ongoing supply ischemia. One mechanism for evaluating this parameter is to determine if STP at t(B) exceeds some predetermined percentage of the value at t(C). That is, if supply ischemia is ongoing, the STPs may decrease from the maximum but should still remain relatively high through the time period B. Thus, if at t(B) the STP is back to baseline or relatively low this would indicate that supply ischemia is not present (either another event such as vasospasm or the supply ischemia has self resolved). Thus, if STP at t(B) is at least 50% of the maximum STP, then the process indicates (970) that supply ischemia is present. The percentage value used may be appropriately selected. The higher the value, the greater the specificity of the process and the less like that a false positive will occur. While non-limiting, values from 40% to 90% in general and specific values of 50%, 75%, and 80% are included.

In general, a sudden, total coronary artery occlusion is serious and if unresolved will likely lead to an acute myocardial infarction. Thus, there is a desire to accurately identify these events and encourage appropriate medical intervention. Conversely, there is also a desire not to generate false positives, unduly worry the patient and burden the caregiver. Thus, as timelines, ranges and parameters are employed, they should be selected to ensure an appropriate reliability threshold.

In some instances, the data will be clearly indicative of a given issue. For example, if the STP changes from one relatively constant value to another relatively constant value in one second, then this is quite likely a postural change. Conversely, if a change occurs over a minute and leads to a relative maximum that remains for an observation period, this is highly suggestive of supply ischemia. When a change occurs more gradually, reaches a peak and returns to a baseline, this is most likely indicative of, for example, demand ischemia during exercise.

There are, of course, parameters that may be closer and harder to distinguish. For example, a vasospasm (a temporary arterial contraction) will lead to an increase in the STP values with a return to baseline. This may be difficult to discern from stable angina (e.g., demand ischemia). Similarly, various factors may cause a more rapid increase (and hence slope) in a demand ischemia case or a less rapid increase in a supply ischemia. For example, an artery may become partially occluded for a brief period and then become fully occluded. The point is that some situations will be harder to discern, particularly based upon the criteria selected for inclusion or exclusion such as the required slope, the percentage of events above threshold, the value at the end of the time period, the time to reach the maximum, etc.

In order to increase the specificity of the analysis, particularly in these closer cases, various embodiments include secondary factors that may be utilized to rule in or rule out a conclusion. FIG. 6D illustrates one such example where the STP data for demand ischemia is plotted against an exemplary heart rate graph. As previously discussed, demand increases as the patient increase their level of exertion. As the coronary artery is unable to provide the necessary supply, angina ensues and the patient becomes unable to continue or maintain the level of exertion. As such, the patient decreases their level of exertion and consequently, demand is reduced. This happens to track well with heart rate. Thus, heart rate monitoring may be used as a secondary factor to confirm demand ischemia or rule out other conclusions. In cases of supply ischemia, vasospasm, or other ST variations there is unlikely to be a direct correlation with heart rate. Other secondary factors may include activity sensors to determine level of exertion or position sensors to identify posture/position. Temperature sensors may be used to detect the ingestion of cold fluids. Pressure sensors may be used to measure blood pressure inside or outside of the heart. Respiration sensors such as impedance sensors may monitor breathing patterns. This may be used to indicate exertion but also shortness of breath may be indicative of an MI. Oxygen saturation may be monitored internally and similarly, tissue perfusion may be monitored by an optical sensor to indicate arterial oxygen supply. Finally, various chemical sensors may be implanted. For example, a potassium imbalance will result in ST variation, typically gradually over time. Thus, potassium is but one substance that may be monitored. Other drugs have known effects on ST values and may be monitored for with embodiments consistent with the teachings of the present invention. C reactive protein is a general indicator of inflammation and if present, might cause borderline data to shift towards supply ischemia. In summary, various other sensor or data inputs may be confirmation of a determination of ST deviation.

Figure 10:
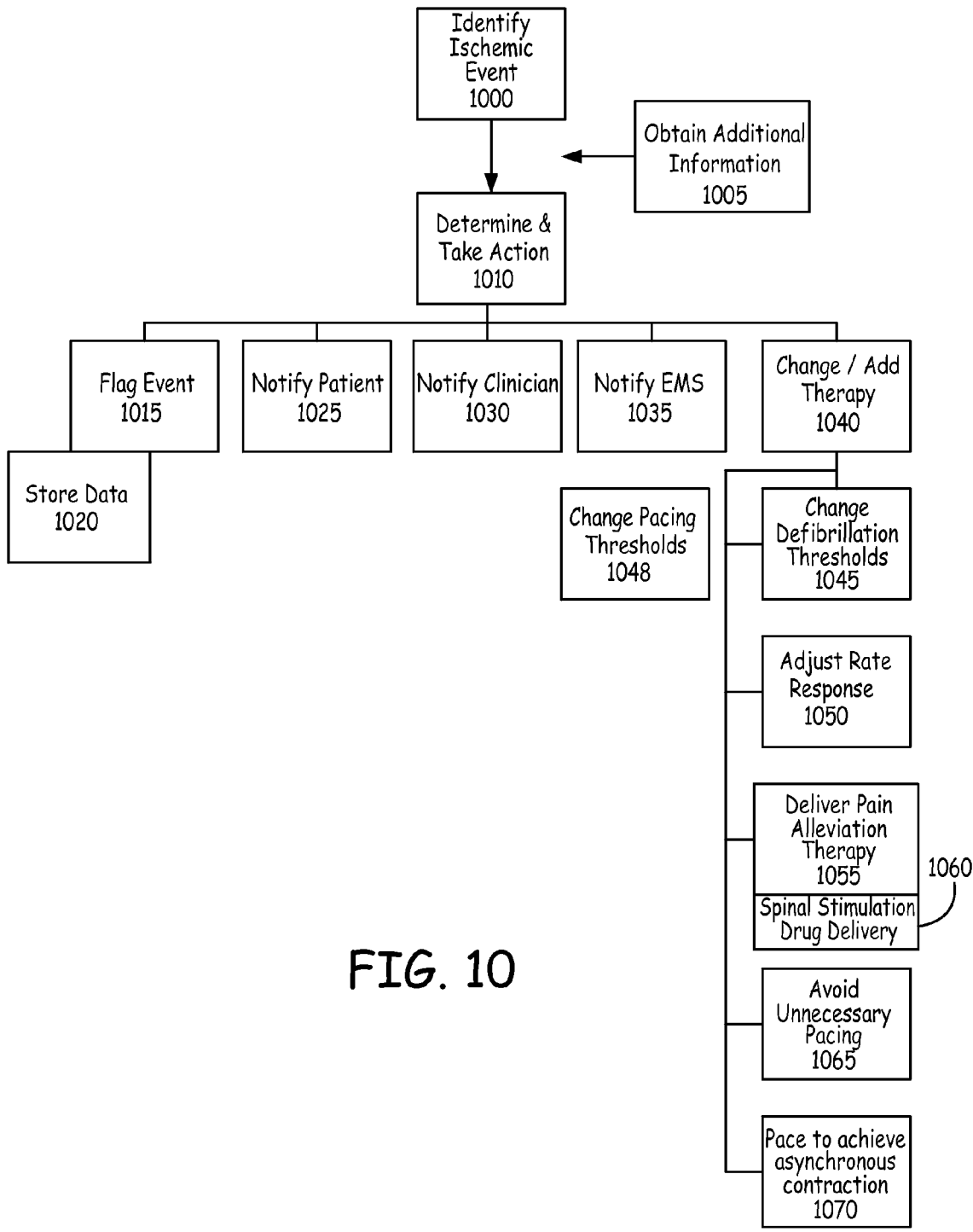

FIG. 10 is a flowchart that illustrates potential actions that may be taken when an ischemic event is identified (1000). Initially, additional information may optionally be collected (1005) to verify a determination (as discussed above), assess a level of severity, determine a patient location, or obtain alternative information including direct patient input. Subsequently, the IMD 10 may determine an appropriate action or set of actions and implement (1010) those actions.

Though not illustrated, in any given situation the IMD 10 may take no action. For example, an event monitored over a period of time that is ultimately determined to be the result of a posture change does not necessarily require any action. The most basic action that the IMD 10 may take is to flag (1015) the event; that is, denote the event in some manner. This will typically include storing data (1020) into memory for future retrieval or use. The data may include the raw data, the STPs, the conclusions, and/or the EGMs in the time period relevant to the event. In some situations, this may be the only action the IMD 10 is capable of providing, but this information may be later retrieved and utilized by a caregiver in any number of contexts.

The IMD 10 may notify (1025) the patient when a detection of ischemia is made. Such notification could occur with an audible sound generated by the IMD 10, a tactile sensation (vibrating), or communication through and external electronic device such as a home monitor, pager, PDA, cellular/digital phone or the like. For demand ischemia, the IMD 10 could notify the patient as exercise levels approach those that have previously caused ischemia. That is, the physical result of demand ischemia will most likely provide an indication to the patient in a time frame that causes them to alter behavior; however, as subsequent events begin the patient could be alerted to avoid the situation. Alternatively, perhaps the demand ischemia is not perceptible or fully disruptive to the patient and such an alert may make them aware of a situation that they would otherwise ignore to some degree.

The potentially more serious situation is supply ischemia. Thus, when the IMD 10 identifies supply ischemia the patient notification (1025) may have more urgency. For example, the patient upon receiving the notification may proceed to an emergency room or request an ambulance. In some cases, there may be predetermined treatments such as taking pharmaceuticals to relax arteries, thin blood, and/or disrupt clots.

The IMD 10 may be communicatively coupled with an external information network. For example, a patient monitor may be coupled with a phone line or computer network or the IMD 10 may communicate directly over a communication pathway like a cellular or digital phone. In such a case, the IMD 10 may communicate (1030) with a clinician and/or communicate (1035) with emergency services to e.g., summon an ambulance.

To this point, the actions taken have been indirect. That is, a determination is made, information is provided, and any subsequent action taken is outside of the IMD itself. Depending upon the IMD's capabilities, various actions may be taken. For example, a therapy may be changed or added (1040). A defibrillation threshold may be adjusted (1045) in response to the noted supply ischemia and potential infarct so that first shock effectiveness is maximized based upon the new condition. Similarly, pacing thresholds may be changed (1048) to provide a greater reliability of capture in anticipation of physiological changes that could occur, otherwise raising the threshold of the tissue.

Another device change could include altering or disabling 1050 rate response (RR). Rate response is the ability of an IPG to vary pacing rate based upon perceived physiological need. With demand ischemia, reducing the upper pacing rate would preclude the heart from reaching a rate deemed undesirable. With supply ischemia, avoiding higher rates would require the heart to work less and hence avoid stressing the heart after this condition is identified.

During either type of ischemia, the patient may experience pain or angina. The IMD 10 may include various pain alleviating mechanisms (1055) such as spinal stimulation or drug delivery (1060). That is, the IMD 10 may include a one-time or replenishable supply of pain relieving drugs, as well as other pharmaceutical or biologic agents. These materials may work to relieve pain, thin the blood, relax the arteries, dissolve occlusions, or promote corrective growth.

Other pacing therapies or variations can also be employed. Similar to adjusting rate response, the IMD 10 may implement an algorithm to reduce or minimize any unnecessary pacing (1065). This is under the assumption that if pacing causes propagation that results in the heart working somewhat harder due to the condition, avoiding such pacing may be beneficial. Pacing may be deemed unnecessary either based on rate; that is, simply pace less or by tolerating intervals (e.g., AV intervals) longer than normal to rely more heavily upon intrinsic conduction.

Another pacing option that the IMD 10 may provide when supply ischemia is detected is to pace to deliberately produce asynchronous contractions (1070). In some cases, this may provide a cardio-protective benefit. In a normal contraction, the ventricles should depolarize and contract in a generally coordinated manner to maximize efficiency and output. If some portion of the heart in infarcted, that tissue no longer depolarizes and contributes to the contraction. Thus, the tissue surrounding the infarction must work that much harder. When there is a synchronized contraction, each portion of the heart muscle is contracting (through fluid) against similarly contracted tissue. In an asynchronous contraction, the contracting portion is contracting against a relaxed portion of the heart. Thus, the contracting portion is not encountering as much resistance and works less. Cardiac output may not be as efficient or optimized, however, as a short term therapy it may prove useful and even as a longer term therapy in some cases.

Various embodiments consistent with the present invention have been illustrated and described. It should be appreciated that the present invention is not limited to the embodiments described nor to the particular arrangement of elements, steps or sequences and one of ordinary skill in the art will understand the variation of the described embodiments are within the spirit and scope of the present invention as set forth in the claims.

The invention claimed is:

1. A method comprising:
   obtaining an electrogram representing cardiac data from an implantable medical device for a plurality of cardiac cycles;
   determining an ST segment data point for each of the cardiac cycles;
   initiating a timer interval when one of the ST segment data point values exceeds a threshold value;
   determining a maximum ST segment data point value during the timer interval;
   determining an amount of time from initiation of the timer interval until the maximum ST segment data point value occurs; and
   determining whether the ST segment data points indicate ischemia based on the amount of time.

2. The method of claim 1, further comprising determining whether the ST segment data points indicate demand ischemia.

3. The method of claim 1, wherein determining an ST segment data point further comprises:
   identifying a peak of an R wave;
   adding a predetermined time interval to the identified peak; and identifying a recorded value at a time identified by the predetermined time interval after the peak of the R wave as the ST segment data point.

4. The method of claim 3, further comprising:
determining a PR isoelectric baseline value; and
subtracting the PR isoelectric baseline value from the recorded value to identify the ST segment data point.

5. The method of claim 1, further comprising:
determining whether the ST segment data points indicate supply ischemia.

6. The method of claim 5, further comprising:
determining that the ST segment data points do not indicate supply ischemia if the amount of time is less than a first short value or greater than a first long value.

7. The method of claim 5, further comprising:
determining that the ST segment data points do not indicate supply ischemia if less than a predetermined percentage of the ST segment data points occurring during the timer interval exceed the threshold value.

8. The method of claim 5, further comprising:
determining that the ST segment data points do not indicate supply ischemia if an ST segment data point occurring at a termination of the timer interval is less than a predetermined percentage of the maximum ST segment data point value.

9. The method of claim 5, further comprising:
calculating a slope of the ST segment data points prior to the maximum ST segment data point; and
determining that the ST segment data points do not indicate supply ischemia if the slope is less than a first slope value.

10. The method of claim 5, further comprising evaluating a secondary indicator to confirm the determination of whether the ST segment data points indicate supply ischemia.

11. The method of claim 1, further comprising:
monitoring the ST segment data point values; and
processing the values using a predetermined filter bank.

12. The method of claim 1, further comprising:
monitoring the ST segment data point values; and
processing the values by comparing to a template.

13. An apparatus comprising:
means for obtaining an electrogram representing cardiac data from an implantable medical device for a plurality of cardiac cycles;
means for determining an ST segment data point for each of the cardiac cycles;
means for initiating a timer interval when one of the ST segment data point values exceeds a threshold value;
means for determining a maximum ST segment data point value during the timer interval;
means for determining an amount of time from initiation of the timer interval until the maximum ST segment data point value occurs; and
means for determining whether the ST segment data points indicate ischemia based on the amount of time.

14. The apparatus of claim 13, further comprising means for determining whether the ST segment data points indicate demand ischemia.

15. The apparatus of claim 13, wherein the means for determining an ST segment data point further comprise:
means for identifying a peak of an R wave;
means for adding a predetermined time interval to the identified peak; and
means for identifying a recorded value at a time identified by the predetermined time interval after the peak of the R wave as the ST segment data point.

16. The apparatus of claim 15, further comprising:
means for determining a PR isoelectric baseline value; and
means for subtracting the PR isoelectric baseline value from the recorded value to identify the ST segment data point, 17. The apparatus of claim 13, further comprising:
means for determining whether the ST segment data points indicate supply ischemia.

18. The apparatus of claim 17, further comprising:
means for determining that the ST segment data points do not indicate supply ischemia if the amount of time is less than a first short value or greater than a first long value.

19. The apparatus of claim 17, further comprising:
means for determining that the ST segment data points do not indicate supply ischemia if less than a predetermined percentage of the ST segment data points occurring during the timer interval exceed the threshold value.

20. The apparatus of claim 17, further comprising:
means for determining that the ST segment data points do not indicate supply ischemia if an ST segment data point occurring at a termination of the timer interval is less than a predetermined percentage of the maximum ST segment data point value.

21. The apparatus of claim 17, further comprising:
means for calculating a slope of the ST segment data points prior to the maximum ST segment data point; and
means for determining that the ST segment data points do not indicate supply ischemia if the slope is less than a first slope value.

22. The apparatus of claim 17, further comprising means for evaluating a secondary indicator to confirm the determination of whether the ST segment data points indicate supply ischemia.

23. An apparatus comprising:
a sensor input that obtains an electrogram representing cardiac data for a plurality of cardiac cycles;
an electrogram analysis module that determines an ST segment data point for each of the cardiac cycles; and
an ST analysis module that:
initiates a timer interval when one of the ST segment data point values exceeds a threshold value;
determines a maximum ST segment data point value during the timer interval;
determines an amount of time from initiation of the timer interval until the maximum ST segment data point value occurs; and
determines whether the ST segment data points indicate ischemia based on the amount of time.

24. The apparatus of claim 23, wherein the ST analysis module determines whether the ST segment data points indicate demand ischemia.

25. The apparatus of claim 23, wherein the electrogram analysis module:
identifies a peak of an R wave;
adds a predetermined time interval to the identified peak; and
identifies a recorded value at a time identified by the predetermined time interval after the peak of the R wave as the ST segment data point.

26. The apparatus of claim 25, wherein the electrogram analysis module:
determines a PR isoelectric baseline value; and
subtracts the PR isoelectric baseline value from the recorded value to identify the ST segment data point.

27. The apparatus of claim 23, wherein the ST analysis module determines whether the ST segment data points indicate supply ischemia.

28. The apparatus of claim 27, wherein the ST analysis module determines that the ST segment data points do not indicate supply ischemia if the amount of time is less than a first short value or greater than a first long value.

29. The apparatus of claim 27, wherein the ST analysis module determines that the ST segment data points do not indicate supply ischemia if less than a predetermined percentage of the ST segment data points occurring during the timer interval exceed the threshold value.

30. The apparatus of claim 27, wherein the ST analysis module determines that the ST segment data points do not indicate supply ischemia if an ST segment data point occurring at a termination of the timer interval is less than a predetermined percentage of the maximum ST segment data point value.

31. The apparatus of claim 27, wherein the ST analysis module:
- calculates a slope of the ST segment data points prior to the maximum ST segment data point; and
- determines that the ST segment data points do not indicate supply ischemia if the slope is less than a first slope value.

32. The apparatus of claim 27, wherein the ST analysis module evaluates a secondary indicator to confirm the determination of whether the ST segment data points indicate supply ischemia.

* * * * *